(12) United States Patent
Ikonen et al.

(10) Patent No.: US 10,681,515 B2
(45) Date of Patent: Jun. 9, 2020

(54) METHOD AND SYSTEM FOR VERIFYING WIRELESS CONNECTION BETWEEN MEDICAL DEVICES

(71) Applicant: GENERAL ELECTRIC COMPANY, Schenectady, NY (US)

(72) Inventors: Emma Elina Ikonen, Helsinki (FI); Kristian Matti Karru, Helsinki (FI); Otto Valtteri Pekander, Helsinki (FI); Erno Petteri Muuranto, Helsinki (FI); Magnus Kall, Helsinki (FI); Ville Petteri Vartiovaara, Helsinki (FI); Henrik Ekman, Helsinki (FI)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/540,426

(22) PCT Filed: Sep. 18, 2015

(86) PCT No.: PCT/US2015/050900
§ 371 (c)(1),
(2) Date: Jun. 28, 2017

(87) PCT Pub. No.: WO2016/108968
PCT Pub. Date: Jul. 7, 2016

(65) Prior Publication Data
US 2018/0013648 A1 Jan. 11, 2018

(30) Foreign Application Priority Data
Dec. 30, 2014 (GB) .................................. 1423332.4

(51) Int. Cl.
*H04W 72/04* (2009.01)
*H04W 4/80* (2018.01)
*H04W 4/38* (2018.01)
*A61B 5/00* (2006.01)
*H04W 4/08* (2009.01)
*H04W 4/18* (2009.01)
*H04L 12/26* (2006.01)
*H04W 24/08* (2009.01)

(52) U.S. Cl.
CPC ............ *H04W 4/80* (2018.02); *A61B 5/0024* (2013.01); *H04L 43/0811* (2013.01);
(Continued)

(58) Field of Classification Search
CPC .... H04L 43/0811; H04W 24/08; H04W 4/008
See application file for complete search history.

(56) References Cited

U.S. PATENT DOCUMENTS 7,693,045 B2 * 4/2010 McGee ............... H04L 43/0811
370/216
10,008,108 B2 * 6/2018 Cho ....................... G08C 17/02
(Continued)

FOREIGN PATENT DOCUMENTS
WO 2005057466 A2 6/2005

OTHER PUBLICATIONS

Li ("Group Device Pairing based Secure Sensor Association and Key Management for Body Area Networks," IEEE Infocom 2010 Proceedings, Mar. 14, 2010) (Year: 2010).*
(Continued)

*Primary Examiner* — Jamal Javaid

(57) ABSTRACT

A method for verifying wireless devices connected to a wireless medical body area network, MBAN, is provided. The method comprises activating a request for verification by a user activating the request for verification on any one of the wireless devices; receiving the request for verification by the any one wireless device of the wireless MBAN; and indicating a plurality of wireless devices connected to the wireless MBAN by displaying an indication on the plurality of wireless devices. A wireless MBAN comprising wireless devices. The wireless MBAN comprises each wireless device being configured for an activation of a verification;
(Continued)

and a plurality of the wireless devices being configured to display an identification upon the activation of the verification.

14 Claims, 3 Drawing Sheets

(52) U.S. Cl.
CPC ............... *H04W 4/08* (2013.01); *H04W 4/18* (2013.01); *H04W 4/38* (2018.02); *H04W 24/08* (2013.01); *A61B 2560/0276* (2013.01)

(56) References Cited

U.S. PATENT DOCUMENTS

2001/0034852 A1\* 10/2001 Kawashima ........ H04L 41/0213
714/4.1

2012/0242501 A1\* 9/2012 Tran ..................... A61B 5/0024
340/870.02

OTHER PUBLICATIONS

International Search Report and Written Opinion for PCT/US2015/050900, dated Nov. 30, 2015, 12 pages.
Combined Search and Exam Report for corresponding GB Appln. No. 1423332.4, dated Jun. 19, 2015, 5 pages.
Li et al., "Group Device Pairing based Secure Sensor Association and Key Management for Body Area Networks," IEEE Infocom 2010 Proceedings, IEEE, Mar. 14, 2010, 10 pages.
Prasad et al., "Efficient Device Paring Using "Human-Comparable" Synchronized Audiovisual Patters" In: "Applied Cryptography and Network Security," ISBN, vol. 5037, 2008, 18 pages.
Li et al., "Body Area Network and Its Standardization at IEEE 802.15.MBAN," 16th 1st Mobile and Wireless Communications Summit, 2007 IEEE, Jul. 1, 2007, 5 pages.

\* cited by examiner

METHOD AND SYSTEM FOR VERIFYING WIRELESS CONNECTION BETWEEN MEDICAL DEVICES

This application is a filing under 35 U.S.C. 371 of international application number PCT/US2015/050900, filed Sep. 18, 2015, which claims priority to GB application number 1423332.4, filed Dec. 30, 2014, the entire disclosures of each are hereby incorporated by reference.

TECHNICAL FIELD

The present disclosure relates to a method and system for verifying wireless connections. More particularly, the present disclosure relates to a method and a system and method for verifying wireless connections between medical devices, for example between a sensor and a host or monitor.

BACKGROUND

Sensors of medical equipment have been connected to the host device through cabling or tubing. This enables the user to verify the connection by following the cable from one device at the end of the cable to the other and device connected to it. In a wireless application there is no physical connection between the host and the sensor. Still, the need to verify the connection remains.

Medical sensors connected to each other through cables making up a network of such devices applied to and around a single patient is called a medical body area network, MBAN. Such a MBAN is used normally in a hospital, but also in other places such as a home or a sport facility. The devices included in and part of an MBAN can easily be seen by the connected cables between the devices. A new device can be connected to an existing MBAN by connecting the cable of the new device to a hub of the existing MBAN.

With wireless applications the communication can be carried out without a physical connection, such as a cable. An example of a wireless MBAN is disclosed in US 2009/0186577 A1. A wireless MBAN may give some advantages. However, it is difficult for a user to see what wireless devices are part of the wireless MBAN, because there are no cables to physically connect between the devices and the host. It is difficult for a user to verify which of the wireless devices are connected to a certain receiving host or monitor. Typically the wireless device may be verified based on the serial number of the devices involved, or the device name, or the patient's identification. This is laborious and slow and requires extreme precision from the user to verify the serial number, device names, or patient identification. Human error and confusion is common in this situation and can lead to very serious consequences. When a verification needs to be made it is normally preferred that it takes place quickly.

It is a problem to verify wireless devices part of a wireless MBAN, especially for increasing the intuitiveness and speed of performing the verification. It is a problem to find out where the data a caretaker sees comes from. It is a problem to ensure that data is collected from a specific patient or person without interference of data collected from somebody else. How to realize a verification in a simple manner and in an intuitive manner is a technical problem. Ease and intuitiveness and security are problems to consider. It is a problem to provide solutions that are economic and technically feasible, a solution must be possible and practical to perform in realty easily and conveniently, also in a medical environment. Medical environments inherently have strict regulations and health and safety aspects to consider.

SUMMARY OF THE INVENTION

The present disclosure is directed to a method for verifying wireless devices connected to a wireless medical body area network, MBAN, and a wireless MBAN. This can be achieved by the features as defined by the independent claims. Further enhancements are characterized in the dependent claims. For this disclosure, medical devices, such as sensors, connected to each other and/or a host and/or a monitor through cables or wirelessly to a network applied to and around a single patient is called a medical body area network, MBAN. This MBAN can be used in a hospital or at home or any other suitable place.

One embodiment provides a method for verifying wireless devices connected to a wireless medical body area network, MBAN. The method comprises activating a request for verification by a user activating the request for verification on any one of the wireless devices; receiving the request for verification by the any one wireless device of the wireless MBAN; and indicating a plurality of wireless devices connected to the wireless MBAN by displaying an indication on the plurality of wireless devices. The plurality of wireless devices may be all wireless device of the wireless MBAN.

According to one embodiment, indicating the plurality of wireless devices connected to the wireless MBAN by displaying the indication on the plurality of wireless devices may be include indicating the plurality of wireless devices connected to a host or monitor of the wireless MBAN, especially indicating the plurality of wireless sensor devices connected to a host or monitor of the wireless MBAN. According to one embodiment, the identification is the same for the plurality of, or all, wireless devices. The identification may be one or a combination of the following: a color, a sequenced flash pattern, a sound, and a symbol.

According to one embodiment, the indication is displayed until a user actively ends the display of the indication, for example by re-activating the request for verification. According to one embodiment, the indication is displayed until a period of time has lapsed.

According to one embodiment, the indication may be an alphanumeric code of one or two or three or four or five or more signs.

One embodiment provides a wireless medical body area network, MBAN, comprising wireless devices. The wireless MBAN comprises each wireless device being configured for an activation of a verification, and a plurality of the wireless devices being configured to display an identification upon the activation of the verification. The plurality of wireless devices may be all wireless device of the wireless MBAN.

According to one embodiment, the identification is the same for the plurality of, or all, wireless devices within the wireless MBAN. The identification may be one or a combination of the following: a color, a sequenced flash pattern, a sound, and a symbol. According to one embodiment, the identification may be an alphanumeric code of one, or two or three or four or five signs, or more. The identification may be a plurality of signs.

According to one embodiment, the wireless devices comprise at least one hub and at least one sensor. According to one embodiment, the wireless devices comprise at least one sensor, and no hub or host. The sensor may be configured for taking on a function as a hub or host. The hub may be configured to list all wireless devices within the wireless MBAN. The hub and/or the sensor may be configured to communicate with a second network, for example the infrastructure of a hospital or any available Wi-Fi.

According to at least one embodiment, a method and a wireless MBAN are provided making it as easy, fast and intuitive as possible to verify a wireless connection between communicating devices through clear matching visual and/or auditory indications on the devices. Both a host device and a sensor device may be able to produce visual and/or auditory indications. Once activated from one, a corresponding indication also appears on the other device or devices involved in the communication. The indication may be for example a color and/or a sequence of blinking activated to be displayed and/or a sound produced similarly on both devices.

According to at least one embodiment, the wireless devices may also communicate with a group of other devices. The indication may be activated from any party communicating through the specified connection. For example if communicating with several sensors at any given time the indication can be activated from the host (e.g. a monitor or patient specific hub device) or a sensor to appear on one or all of the sensors.

According to at least one embodiment, a solution is provided for verifying the connection giving visual and/or auditory indications on the communicating devices. Alone, or merged with existing systems, a technical effect of increase in intuitiveness and speed of performing the verification is achieved.

At least one of the above embodiments provides one or more solutions to the problems and disadvantages with the background art. Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any other claimed embodiment(s).

BRIEF DESCRIPTION OF THE DRAWINGS

The accompanying drawings illustrate presently exemplary embodiments of the disclosure and serve to explain, by way of example, the principles of the disclosure.

DETAILED DESCRIPTION

Figure 1:
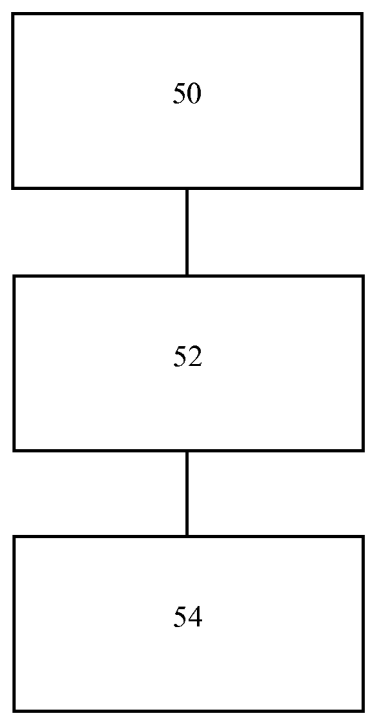
FIG. 1 shows a flow chart of a method according to an exemplary embodiment of the disclosure.

FIG. 1 discloses an exemplary embodiment of a method for verifying wireless devices connected to a wireless medical body area network, MBAN. The wireless MBAN may be located in a hospital, but may be located at home, a sport facility, or any other place. The method comprises the following steps taken in order. A first step 50 may be activating a request for verification by a user activating the request for verification on any one of the wireless devices. The activation may be made on any wireless device, for example a hub, a host, or a sensor. The activation may not be limited to be made only from the host, but from any available wireless device part of the wireless MBAN. This provides a technical effect of a user being able to activate a verification directly from a sensor. A second step 52 may be receiving the request for verification by the any one wireless device of the wireless MBAN. The wireless device that the user selects for activating the request receives the request for verification. A third step 54 may be indicating a plurality of wireless devices connected to the wireless MBAN by displaying an indication on the plurality of wireless devices. The wireless device that received the request for verification may be configured for arranging a plurality of wireless devices within the wireless MBAN to display an indication. Hereby the plurality of wireless devices within the wireless MBAN displays an indication that verifies the wireless devices part of the wireless MBAN. The plurality of wireless devices may be only two wireless devices, or any number of wireless devices, or all wireless devices. The plurality of wireless devices may be only sensors, or one or more sensors and a host, or one or more sensors and a monitor. However, it may be wireless devices part of the wireless MBAN, because the verification may be to know if a wireless device is part of a certain wireless MBAN. The verification may verify that a connection exists and that one or more sensors are paired to a host or monitor receiving data, and/or may verify which host or monitor one or more sensors are connected to so that a user can see that the sensors are connected to the right host or monitor.

According to one embodiment, a host device within a wireless MBAN may display a list of wireless devices currently communicating within the wireless MBAN. Upon activating and receiving the verification request on any one of the wireless devices (for example hosts or sensors) a plurality, or all, wireless devices of the MBAN are indicated. According to one embodiment, indicating the plurality of wireless devices connected to the wireless MBAN by displaying the indication on the plurality of wireless devices may include indicating the plurality of wireless devices connected to a host or monitor of the wireless MBAN. For example, indicating the plurality of wireless sensor devices connected to a host or monitor of the wireless MBAN, allows a user to verify what sensors are connected to a certain host or monitor.

According to one embodiment, the identification is the same for the plurality of, or all, wireless devices. The identification may be one or a combination of the following: a color, a sequenced flash pattern, a sound, and a symbol. In this way a user may quickly and intuitively verify what wireless devices are part of the wireless MBAN. For example, it can be verified if a sensor connected to a patient is actually part of the wireless MBAN for that patient or not and if the sensor is connected to a specific host or monitor.

According to one embodiment, the indication may be displayed until a user actively ends the display of the indication, for example by re-activating the request for verification. In this way the user can activate the verification and the resulting indication last until the user decides to end it, for example by activating the request again. According to one embodiment, the indication is displayed until a period of time has lapsed. In this way a request for verification causes the wireless devices to display their indication for a specific pre-set time, for example 5 or 10 seconds.

According to one embodiment, the identification is an alphanumeric code. The alphanumeric code may be made up of one, or two, or three, or four, or five, or more characters. In this way it can quickly be verified what wireless devices are within a certain wireless MBAN.

Figure 2:
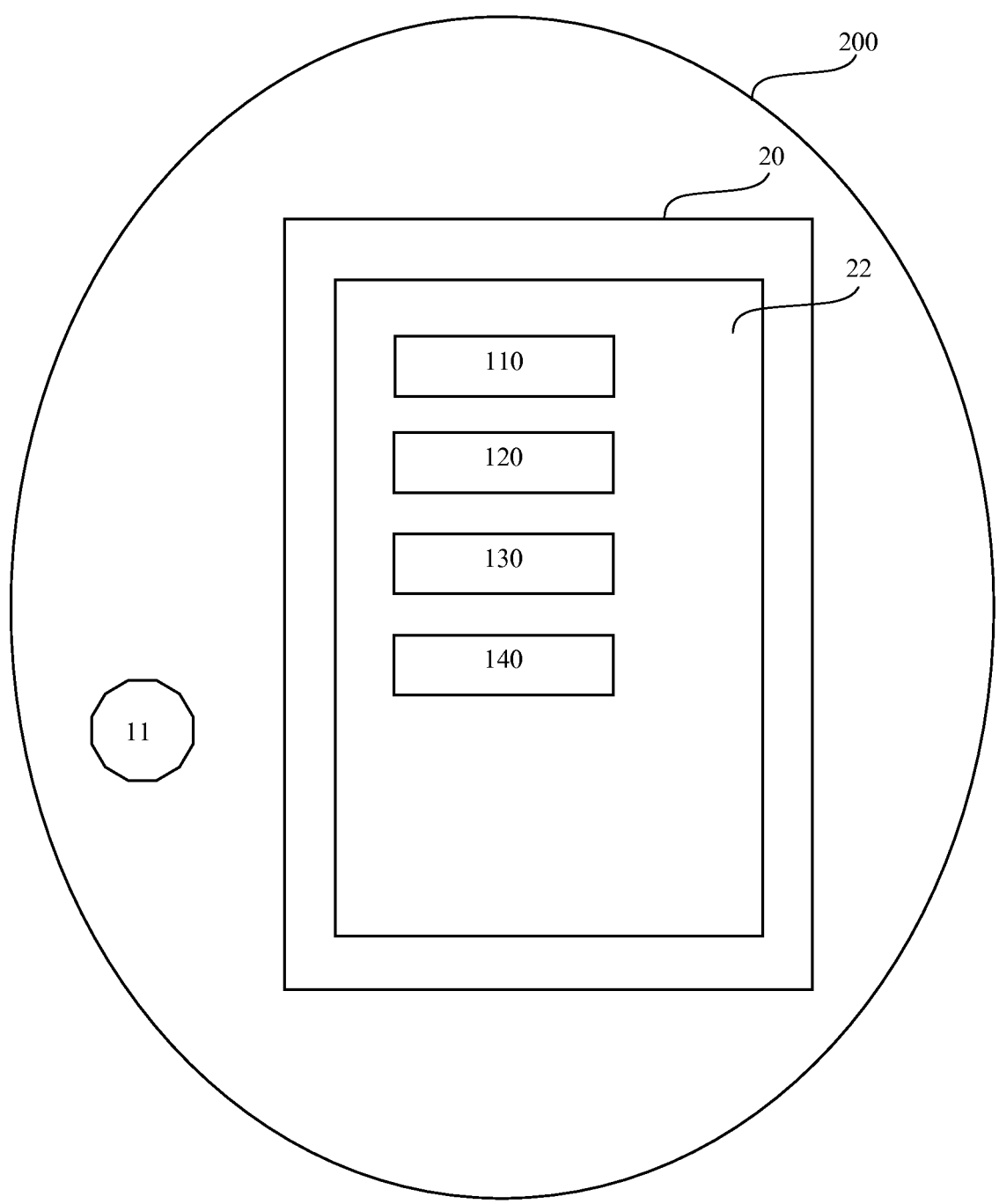
FIG. 2 is a diagrammatic illustration of a wireless MBAN according to an exemplary embodiment of the disclosure.
Figure 3:
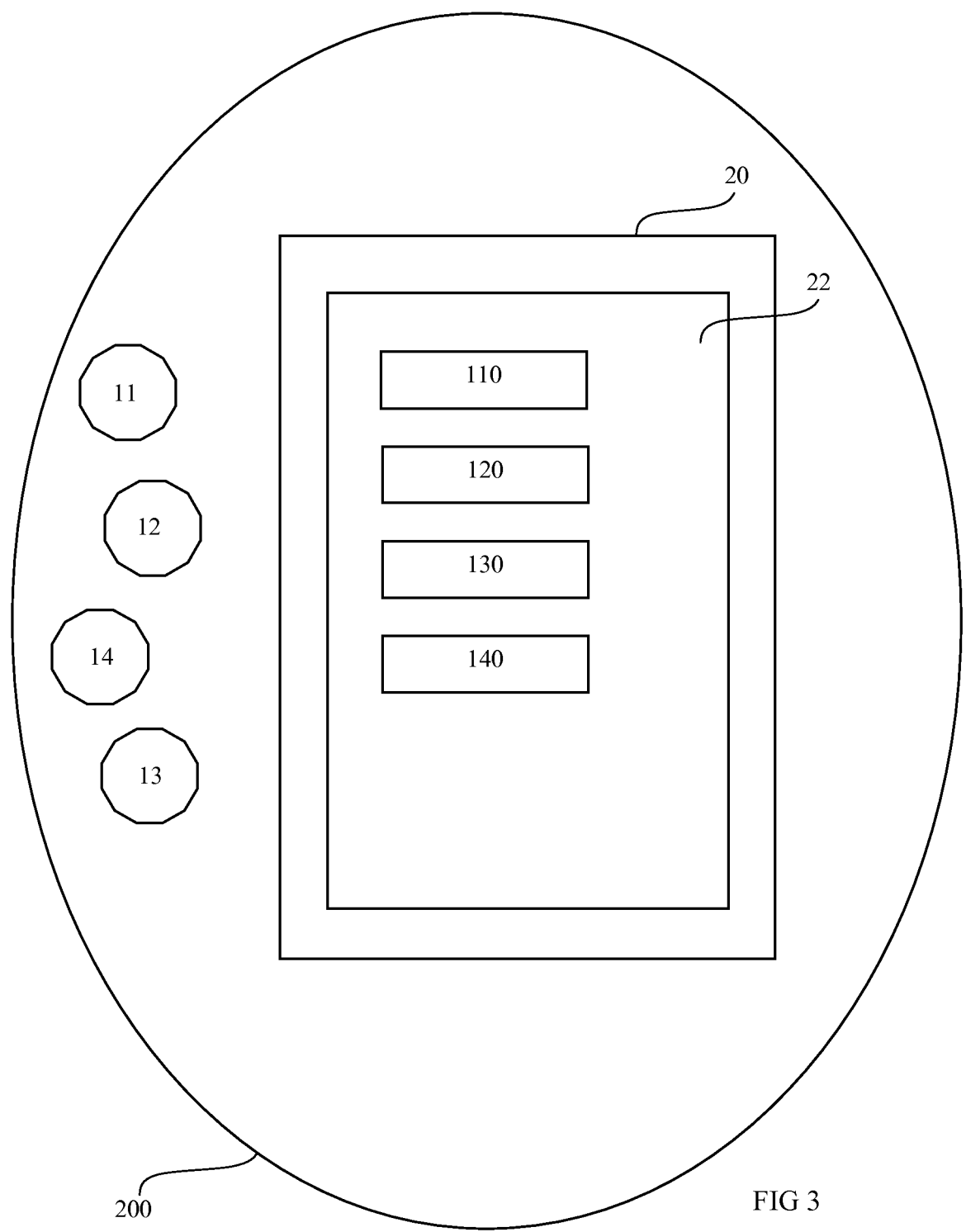
FIG. 3 is a diagrammatic illustration of a wireless MBAN according to an exemplary embodiment of the disclosure.

According to one embodiment, a wireless medical body area network, MBAN, comprises wireless devices. The wireless devices may for example only be sensors, or in another example sensors and at least one host. The wireless MBAN may comprise each wireless device being configured for an activation of a verification, and a plurality of the wireless devices being configured to display an identification upon the activation of the verification. The plurality of wireless devices may be two or more or all wireless devices within the wireless MBAN. As may be taken from FIG. 2, a wireless device, a host 20 in this example, may have a screen 22 with a list 110, 120, 130, 140 of wireless devices. A wireless device 11, a sensor in this example, may be part of the wireless MBAN 200. A user may activate a wireless device to request a verification. This may be any wireless device on the list 110, 120, 130, 140 or the wireless device 11. When the wireless device receives the request for verification, then a plurality of the wireless devices, for example all the wireless devices of the wireless MBAN display an identification. This may for example be taken from FIG. 3, where a host 20 displays identifications for the wireless devices 110, 120, 130, 140 on the screen 22. All the wireless devices 11, 12, 13, 14, 20 of the wireless MBAN 200 display an identification allowing a user to verify that they are all part of the wireless MBAN 200.

According to one embodiment, the identification is the same for all wireless devices within the wireless MBAN. The identification may be one or a combination of the following: a color, a sequenced flash pattern, a sound, and a symbol. This has as a technical effect that it can quickly and intuitively be verified what wireless devices are part of a certain wireless MBAN.

According to one embodiment, the wireless devices comprise at least one sensor acting as a hub. In such an embodiment, no host or hub need to be present, instead a sensor can be configured to take on the functions of a hub and/or host. In one embodiment, the wireless devices comprise at least one hub and at least one sensor. The hub may be configured to list all wireless devices within the wireless MBAN.

According to one embodiment, the identification is an alphanumeric code. The alphanumeric code may be made up of one, or two, or three, or four, or five, or more characters. In this way it can quickly be verified what wireless devices are within a certain wireless MBAN.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for verifying wireless devices connected to a wireless medical body area network (MBAN), the method comprising:
   activating a request for verifying wireless devices which have been connected to the MBAN by a user activating the request on any one of the wireless devices;
   receiving the request for verification by the any one wireless device of the wireless MBAN; and
   indicating a plurality of wireless devices which have been connected to the wireless MBAN by displaying an indication on each of the plurality of wireless devices.

2. The method of claim 1, wherein the indication is the same for the plurality of wireless devices.

3. The method of claim 1, wherein the indication is one or a combination of the following: a color, a sequenced flash pattern, a sound, and a symbol.

4. The method of claim 1, wherein indicating the plurality of wireless devices connected to the wireless MBAN by displaying the indication on each of the plurality of wireless devices includes indicating the plurality of wireless devices connected to a host or monitor of the wireless MBAN.

5. The method of claim 1, wherein the indication is displayed until a user actively ends the display of the indication.

6. The method of claim 1, wherein the indication is displayed until a period of time has lapsed.

7. The method of claim 1, wherein the indication is an alphanumeric code.

8. A wireless medical body area network (MBAN) comprising:
   wireless devices, each wireless device being configured to:
      receive a request for verifying wireless devices which have been connected to the wireless MBAN; and
      make a plurality of the wireless devices which have been connected to the wireless MBAN each display an identification upon the request for verification.

9. The wireless MBAN of claim 8, wherein the identification is the same for the plurality of wireless devices within the wireless MBAN.

10. The wireless MBAN of claim 8, wherein the identification is one or a combination of the following: a color, a sequenced flash pattern, a sound, and a symbol.

11. The wireless MBAN according to claim 8, wherein the wireless devices comprise at least one sensor acting as a hub.

12. The wireless MBAN according to claim 8, wherein the wireless devices comprise at least one hub and at least one sensor.

13. The wireless MBAN of claim 12, wherein the hub is configured to list all wireless devices within the wireless MBAN.

14. The wireless MBAN of claim 8, wherein the identification is an alphanumeric code.

* * * * *